US006784194B2

(12) United States Patent
Lallement et al.

(10) Patent No.: US 6,784,194 B2
(45) Date of Patent: *Aug. 31, 2004

(54) THERAPEUTIC USE OF A THIENYLCYCLOHEXYLAMINE DERIVATIVE

(75) Inventors: Guy Lallement, Seyssins (FR); Pierre D'Arbigny, Courbevoie (FR); Jean-Marc Kamenka, Montpellier (FR)

(73) Assignee: Societe de Conseils de Recherches et D'Applications Scientifiques (S.C.R.A.S.) (FR)

( * ) Notice: Subject to any disclaimer, the term of this patent is extended or adjusted under 35 U.S.C. 154(b) by 10 days.

This patent is subject to a terminal disclaimer.

(21) Appl. No.: 09/834,552

(22) Filed: Apr. 13, 2001

(65) Prior Publication Data

US 2001/0056091 A1 Dec. 27, 2001

Related U.S. Application Data

(60) Continuation-in-part of application No. 09/180,384, filed on Jan. 11, 1999, now Pat. No. 6,207,685, which is a division of application No. 09/189,887, filed as application No. PCT/FR97/02219 on Dec. 5, 1997, now abandoned.

(30) Foreign Application Priority Data

Dec. 6, 1996 (FR) .............................. 96 14996
Jun. 13, 1997 (FR) .............................. 97 07361

(51) Int. Cl.$^7$ ...................... A61K 31/425; A61K 31/55; A61K 31/44; A61K 31/40

(52) U.S. Cl. ...................... 514/336; 514/216; 514/219; 514/358; 514/414

(58) Field of Search .................... 514/336, 216, 514/219, 358, 414

(56) References Cited

U.S. PATENT DOCUMENTS 5,179,109 A * 1/1993 Kamenka et al. ............ 514/326
6,207,685 B1 * 3/2001 Lallement et al. .......... 514/336

OTHER PUBLICATIONS

Michaud et al. 'Homochiral structures derived from 1-[1-(2-thienyl)cyclohexyl]piperidine(TCP) are potent non-competitive antagonists of glutamate at NMDA receptor sites' 1994, European J. Med. Chem. vol. 29, p. 869–976.*
Medline Abstract, AN 89143311, 1989, Green et al.*
Medline Abstract, AN 93386465, 1993, Lallement et al.*

* cited by examiner

*Primary Examiner*—Shengjun Wang
(74) *Attorney, Agent, or Firm*—Muserlian, Lucas and Mercanti

(57) ABSTRACT

A method of inhibiting effects of exogenous neurotoxic or neurotoxinic products in warm-blooded animals comprising administering to warm-blooded animals before exposure to said products an inhibitorily effective amount of reversible cholinesterase inhibitor selected from the group consisting of pyridostigmine and physostigmine followed by administration of an inhibitorily effective amount of 2-methyl-1-(1-piperidinyl)-1-(2-thienyl)-cyclohexane in substantially pure racemic, diastereoisomeric or enantiomeric form.

7 Claims, 3 Drawing Sheets

THERAPEUTIC USE OF A THIENYLCYCLOHEXYLAMINE DERIVATIVE

PRIOR APPLICATION

This application is a division of U.S. patent application Ser. No. 09/189,887 filed Nov. 11, 1998, now abandoned, which is a continuation-in-part application of U.S. patent application Ser. No. 09/180,384 filed Jan. 11, 1999, now U.S. Pat. No. 6,207,685 which is the national phase of PCT application PCT/FR97/02219 filed Dec. 5, 1997 claiming the benefit of French Application Serial No. 96/14996 filed Dec. 6, 1996 and Ser. No. 97/07361 filed Jun. 13, 1997.

The present invention relates to the use of a thienylcyclohexylamine, by itself or in combination with other substances with a pharmaceutical activity, for the preparation of a medicament intended to limit or inhibit the effects due to neurotoxic products or those containing neurotoxin. The invention also relates to a product containing a thienylcyclohexylamine and at least one anticholinergic, anticonvulsive or cholinesterase reactivator, and a pharmaceutical composition containing it. This product is also particularly useful for its activity of limiting or inhibiting the effects due to neurotoxic products or those containing neurotoxin.

The family of neurotoxic products or those containing neurotoxin includes products such as the organophosphates which can be found, for example, in insecticides or pesticides for domestic or industrial use, but also poison gas for use in warfare, such as soman, sarin, tabun or VX. Among the existing therapies such as polymedication to combat intoxication by such compounds, none totally prevents the appearance of neuropathological after-effects.

A subject of the invention is the use of thienylcyclohexylamine corresponding to the formula 2-methyl-1-(1-piperidinyl)-1-(2-thienyl) cyclohexane, for the preparation of a medicament intended to limit or inhibit the effects due to neurotoxic products or those containing neurotoxin in primates and in particular in man. It can be used by itself or in combination with other substances with a pharmaceutical activity capable of limiting or inhibiting the effects due to neurotoxic products or those containing neurotoxin.

Thienylcyclohexylamine as defined above, is described in Patent EP 396734. Taking into account the existence of 2 asymmetric carbons, this thienylcyclohexylamime can be in substantially pure racemic, diastereoisomeric or enantiomeric form. The cis diastereoisomer (named gacyclidine) is the preferred compound.

The preparation of the diastereoisomers of 1-thienylcyclohexylamine consists of reacting the 2-bromothienyl-magnesium compound on 2-methylcyclo hexanone, and treating the 2-methyl-1-(2-thienyl) cyclohexanol thus obtained with $NaN_3$ in order to obtain the corresponding azide, reducing this azide into the amine and finally treating with 1,5-halogenopentane. The cis and trans diastereoisomers are separated by preparative chromatography on silica gel, using a hexane/ether mixture (95/5 by volume): the first fraction, corresponding to the trans compound, crystallizes at 40–41° C.; the second fraction, corresponding to the cis compound, crystallizes at 80–81° C. The enantiomers can be obtained by using optically active acids such as di-O,O'-4-toluoyltartaric acid.

A particular subject of the invention is the use of thienylcyclohexylamine as defined above, with at least one substance chosen from anticholinergic, anticonvulsive substances and substances which reactivate cholinesterases.

A particular subject of the invention is the use of thienylcyclohexylamine as defined above, with at least one anticholinergic substance, at least one anticonvulsive substance and at least one substance which reactivates cholinesterases.

The pharmacological terms used have the standard meaning known to a person skilled in the art. Therefore, among the anticholinergic substances, the following substances can be mentioned: atropine, scopolamine, atropine N-oxide, dihexyverine and tiemonium methylsulphate. Among the anticonvulsive substances, the following substances can for example be mentioned: phenobarbital, primidone, carbamazepine, ethosuximide, phenytoin, sodium valproate, progabide, gabapentin, vigabatrin, loprazolam, benzodiazepins such as clonazepaim, clobazam, diazepam and prodiazepam. Among the substances which reactivate cholinesterases, there can be mentioned pralidoxime, obidoxime, HI6.

A subject of the invention is also a use of thienylcyclohexylamine as defined above, characterized in that the thienylcyclohexylamine is combined with a reversible cholinesterase inhibitor intended to be administered before exposure to neurotoxic products or those containing neurotoxin. Among the reversible cholinesterase inhibitors, the following can be mentioned: pyridostigmine, physostigmine.

The thienylcyclohexylamine as defined above and the other susbtances as above defined are combined for simultaneous use, separate use or use spread over time.

A subject of the invention is also, as a medicament, a product containing thienylcyclohexylamine as defined above, combined with at least one substance with a pharmaceutical activity capable of limiting or inhibiting the effects due to neurotoxic products or those containing neurotoxin, as well as the pharmaceutical compositions containing it.

A more particular subject of the invention is, as a medicament, a product containing thienylcyclohexylamine as defined above, in substantially pure racemic, diastereoisomeric or enantiomeric form, combined with at least one substance chosen from anticholinergic, anticonvulsive substances and substances which reactivate cholinesterases. Preferably, the product as defined above, contains thienylcyclohexylamine as defined above, combined with at least one anticholinergic substance, one anticonvulsive substance and one substance which reactivates cholinesterases. A medicament corresponding to a combination product as defined above is for simultaneous use, separate use or use spread over time.

The invention also relates to a product containing thienylcyclohexylamine and at least one substance chosen from anticholinergic, anticonvulsive substances and substances which reactivate cholinesterases as a combination product for simultaneous use, separate use or use spread over time, to limit or inhibit the effects due to neurotoxic products or those containing neurotoxin.

A subject of the invention is also a product as defined above characterized in that in addition it contains a reversible cholinesterase inhibitor intended to be administered before exposure to neurotoxic products or those containing neurotoxin.

Thienylcyclohexylamine as defined above, can be administered at a dose comprised between 0.001 and 10 mg/kg, preferably between 0.01 and 1 mg/kg. The substances which are optionally combined with it such as anticholinergic, anticonvulsive substances, substances which reactivate cholinesterases or reversible cholinesterase inhibitors, known in pharmacology, are administered at doses usually recommended in their respective pharmacological fields.

Thienylcyclohexylamine as defined above as well as the pharmaceutically active substances with which it is optionally-combined, can be administered by standard administration routes such as oral, intramuscular, intraperitoneal, sub-cutaneous or intravenous. They can be administered simultaneously or separately, by identical or different administration routes. Preferably, thienylcyclohexylamine is administered by intravenous route and the pharmaceutically-active substances with which it is optionally combined such as the anticholinergic, anticonvulsive substances and the substances which reactivate cholinesterases, are administered by intramuscular or intravenous route. In the case where thienylcyclohexylamine is combined with at least one of the pharmaceutically active substances as defined above, the administration of thienylcyclohexylamine can be deferred with respect to the administration of these other substances.

When thienylcyclohexylamine is combined with a reversible cholinesterase inhibitor, it may be administered from the moment of intoxication up to several hours after this intoxication. Preferably, this administration is carried out within two hours of the intoxication. More preferably, this administration can be carried out between 10 minutes and 45 minutes after intoxication.

When thienylcyclohexylamine is not combined with a reversible cholinesterase inhibitor, it may be administered from the moment of intoxication up to 60 minutes after the intoxication and preferably up to 40 minutes after intoxication, and more preferably 30 minutes after intoxication.

The results shown hereafter in the experimental part, first and second series of experiments, illustrate the high effectiveness of the complementary administration of gacyclidine 10 to 45 minutes after intoxication and a pre-administration of a cholinesterase inhibitor. The results shown hereafter in the experimental part, third series of experiments, illustrate the high effectiveness of the complementary administration of cis-thienylcyclohexylamine 30 minutes after intoxication and without a pre-administration of a cholinesterase inhibitor.

Total EEG power (E) during periods B to: is expressed as percentage of baseline value measured during period A status epilepticus appeared about 12 minutes after soman exposure and persisted for 1 H 30. This was followed by a post-critical phase before progressive return to normal pattern. Very similar results were obtained in the other animal treated under the same conditions (total of 2 animals).

Figure 2:
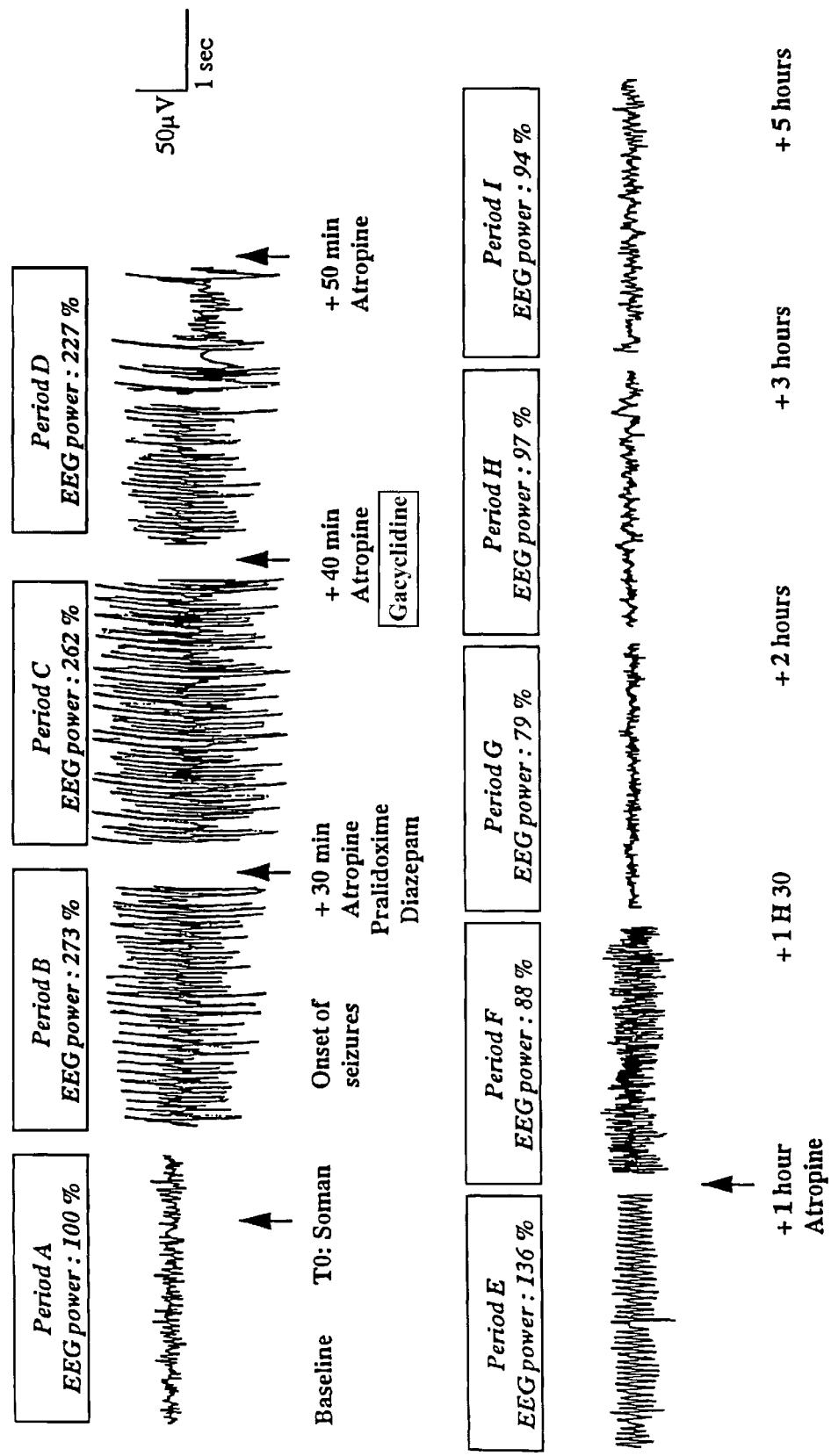

FIG. 2 Representative electroencephalographic (EEG) recordings and EEG total power from a primate poised with 2 $LD_{50}$ of soman which exhibited intense status epilepticus before being treated with atropine/diazepam/pralidoxime 30 minutes together with gacyclidine 30 minutes after poisoning.

Figure 1:
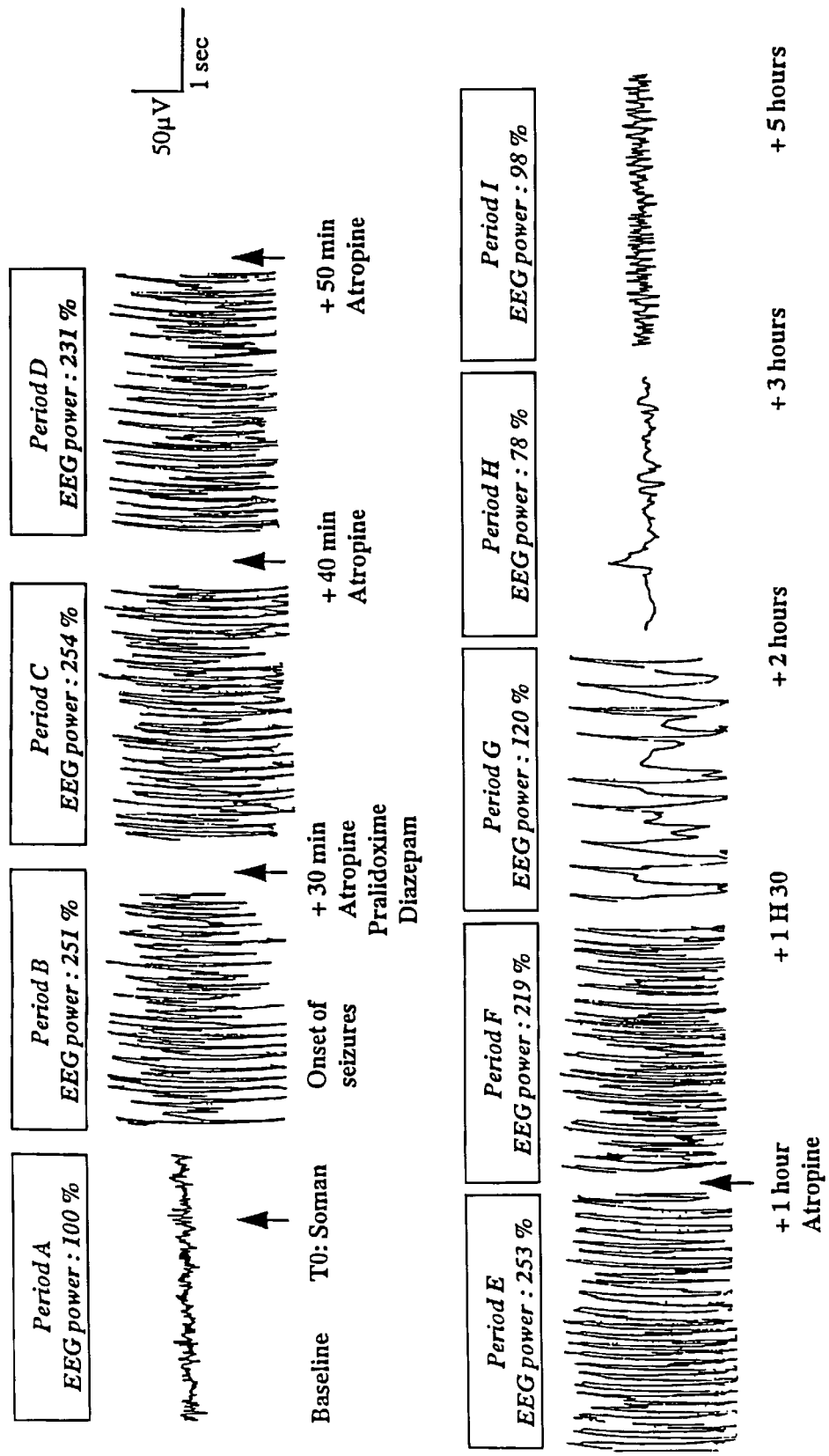
FIG. 1. Representative electroencephalographic (EEG) recordings and EEG total power from a primate poised with 2 $LD_{50}$ of soman which exhibited intense status epilepticus before being treated with atropine/diazepam/pralidoxime 30 minutes after poisoning.

Total EEG power (E) is expressed as in FIG. 1. Status epilepticus appeared about 14 minutes after soman exposure and persisted for 35 to 40 minutes. This was followed by a typical phase with high frequency/low voltage pattern before progressive return to normal EEG activity. Very similar results were obtained in the other animal treated under the same conditions (total of 2 animals)

Figure 3:
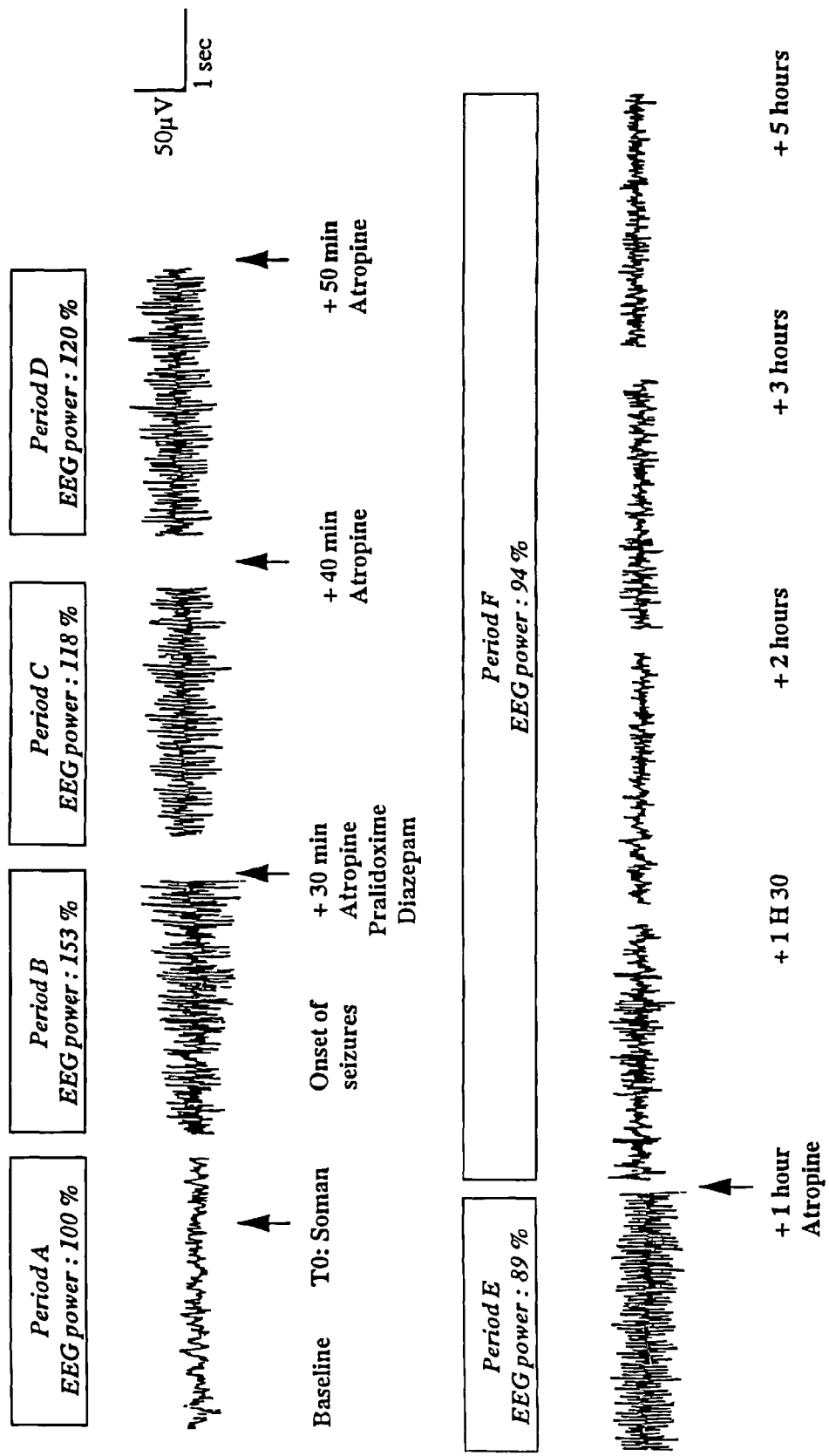

FIG. 3 Representative electroencephalographic (EEG) recordings and EEG total power from a primate poised with 2 $LD_{50}$ of soman which exhibited intense status epilepticus before being treated with atropine/diazepam/pralidoxime 30 minutes after poisoning.

Total EEG power (E) is express as in FIG. 1. The epileptic pattern with only low voltage appeared within 16 minutes and persisted for about 1 hour after poisoning before progressive return to normal EEG activity.

The following examples are presented to illustrate the above procedures and must in no way be considered as limiting the scope of the invention.

EXPERIMENTAL PART

Pharmacological Study
1) First series of Experiments
1a) Study Protocol

Nine Cynomolgus monkeys were treated 1 hour before intoxication with pyridostigmine (0.2 mg/kg; i.m.). This pyridostigmine dose inhibits 30% of the plasmatic cholinesterases, which corresponds to protection standards accepted in NATO countries. The animals are then intoxicated with 5 $LD_{50}$ of soman, organophosphate compound (30 mg/kg; i.m.) then treated 1 minute after intoxication with the "therapeutic cocktail": atropine sulphate (0.5 mg/kg; i.m.)+valium (0.2 mg/kg; i.m.)+pralidoxime (30 mg/kg; i.m.). This mixture of 3 drugs corresponds to the emergency therapy established for personnel in the form of autoinjectable syringes.

Ten minutes after intoxication, the animals receive the gacyclidine by i.v. route (0.01; 0.03 and 0.1 mg/kg, 3 animals per dose).

The animals (unrestrained) are then observed, signs of acute toxicity and recovery are noted over 17 observation periods ranging from 2 minutes post intoxication up to 3 weeks. Three weeks after intoxication, the animals are sacrificed, the brain is removed then, after immersion for 1 month in formalin, histological sections (10 mm) are carried out stained with Luxol Fast Blue HE in order to research the possible neuropathological after-effects.

Similar experiments were carried out on control animals which did not receive gayclidine. Thus, it was possible to see the influence of this compound on the clinical signs of intoxicated animals and on the neuropathological after-effects.

1b) Results
Control Animals (n=4)

In these animals, severe signs of intoxication were noted (muscular fasciculations, trembling, chewing) which appear within 1 to 2 minutes after administration of the soman, the animals then have tonico-clonic convulsions combined with an opisthotonos. Then all the animals fall rapidly into a coma over approximately 5 minutes. The animal's coma lasts from 20 to 40 minutes. After this coma phase, the animals slowly recover over 6 hours following the intoxication, trembling gradually ceases. One day after intoxication, all the animals are capable of walking, clutching and climbing but they only recover normal activity 4 days after intoxication. Three weeks after intoxication, the histopathological examination of cerebral tissues shows a marked neuronal depopulation in the second layer of the frontoparietal cortex in all the primates.

Animals Treated with Thienylcyclohexylamine (n=3 Per Dose)

I.v. administration of gacyclidine is carried out, as indicated in the protocol of the study, during the coma phase of the animal. Observation of the clinical state is summarized in the following table:

| Dose of gacyclidine (mg/kg) | Signs of acute toxicity identical to controls | Prevention of respiratory disorders | Rapid cessation of tremors | A-taxia | Recovery time (controls 4 days) |
|---|---|---|---|---|---|
| 0.1 | X | X | X | X | 4 days |
| 0.003 | X | X | X | | 4 days |
| 0.01 | X | | | | 24 hours no relapse at 48 hours |

Three weeks after intoxication, histological examination of the cerebral tissues of the animals treated with gacyclidine shows a normal neuronal density in the layer II of the frontoparietal cortex, whatever dose of gacyclidine is used. The counts carried out in this cerebral region indicate a significant difference between the neuronal density observed in the control animals and that of the animals treated with gacyclidine. Therefore, there is a neuroprotector effect of the gacyclidine which appears with the lowest dose.

1c) Conclusion

Under our experimental conditions, the emergency treatment was administered 1 minute after intoxication. Under these conditions, the epileptic state triggered by the soman lasts only 3 to 5 minutes. Nevertheless, the neuropathological after-effects remain 3 weeks after intoxication. Administration of gacyclidine in addition to the emergency polymedication allows, at a dose of 0.01 mg/kg i.v., to appreciably increase the recovery of intoxicated animals 48 hours after administration of soman and to prevent the neuronal rarefaction observed in the frontoparietal cortex of the control animals.

2) Second Series of Experiments

The series of experiments described hereafter is close to a real situation. The protocol adopted is as follows:

Animals intoxicated with 8 $LD_{50}$ only receive the equivalent of one single autoinjectable syringe containing atropine sulphate, valium and pralidoxime 1 minute after intoxication. The gacyclidine is administered 45 minutes later by i.v. route; this delay of 45 minutes being assumed to correspond to the time necessary to recover a wounded person, then to transport them to a first aid post where their clothes would be decontaminated by a specialized team and an i.v. injection line set up by medical personnel.

2a) Study Protocol

One month before the experiment, 6 Cynomolgus monkeys are operated on in order to allow the implanting of cortical electrodes for recording the EEG according to a standardized protocol (Mistress et al., Sci. Tech. Anim. Lab., 1984, 9, 35–46). Suitable post-operative care (generalized antibiotherapy for 10 days and local application of antiseptic for 5 days) is carried out.

The day before the experiment, the animals are anaesthetised (Imalgene, 3 mg/kg, im) then placed in a restraining seat. Twenty-four hours later (time necessary for the elimination of more than 99% of the Imalgene), the primates are connected to an EEG recorder (ALVAR 16 canals). The EEG activity of the animals is recorded continuously for 6 hours and analysis of the energy distribution by frequency bands is carried out after FFT analysis (delta band 0.5–5 Hz, theta band 5–10 Hz, alpha band 10–16 Hz, beta band 16–48 Hz) in order to allow the calculation of an EEG index (% delta+theta/% beta). The animals are pre-treated with pyridostigmine (0.2 mg/kg, im) 1 hour before intoxication with soman. This dose of pyridostigmine inhibits 30% of the plasmatic cholinesterases, which corresponds to protection standards accepted in NATO countries. The animals are then intoxicated with 8 $LD_{50}$ of soman, organophosphate compound (30 µg/kg; i.m.) then treated 1 minute after intoxication with the mixture: atropine sulphate (0.25 mg/kg; i.m.)+valium (0.1 mg/kg; i.m.)+pralidoxime (15 mg/kg; i.m.). These doses, in primates, are equivalent to the administration in man of one single autoinjectable syringe. The animals are then observed and the presence or absence in each animal of 5 signs of acute toxicity (trembling, clonisms or tonico-clonic crises, coma, respiratory problems, hyperreactivity to sonorous or tactile stimuli) as well as 4 signs of recovery (ocular reflex, biting reflex, clutching, visual ability to follow movement) are noted 2, 5, 10, 15, 30, 45 minutes after intoxication.

Forty-five minutes after intoxication, 3 animals are treated with gacyclidine, administered by i.v. route at a dose of 0.1 mg/kg. The 3 other animals do not receive treatment. The signs of toxicity and recovery mentioned previously are then noted for each animal 1 hr, 1 hr 15 min, 1 hr 30 min, 1 hr 45 min, 2 hrs, 2 hrs 30 min, 3 hrs 30 min, 4 hrs, 4 hrs 30 min, 5 hrs post-intoxication. Five hours after intoxication (i.e. 6 hours after the start of the experiment taking into account the time for pre-treatment with pyridostigmine), the recording of the animal's EEG activity is stopped, the primates are removed from the restraining seat then transferred (without anaesthetic) into a cage with large dimensions. The clinical state of the animals is then assessed 5 hrs, 5 hrs 30 min, 6 hrs then 24 hrs, 48 hrs, 3 days, 4 days, 1 week, 2 weeks, 3 weeks post-intoxication for the same signs of acute toxicity and recovery as those mentioned previously to which are added the presence or absence of prostration (sign of toxicity), as well as their capacity to sit up, to walk and climb and to feed (signs of recovery).

Three weeks after intoxication, the animals are sacrificed by an i.v. injection of pentobarbital, the brain is rapidly removed and placed in 10% formalin for 1 month (change of bath every week). At the end, histological examination of the cerebral tissues is carried out after staining with Hemalun-eosin/luxol Fast-Blue.

2b) Results

The First Forty-five Minutes Post-intoxication (Before Administration of Gacyclidine, Period $P_1$)

Clinical Signs

In all animals, signs of severe intoxication were noted (muscular fasciculations, trembling, chewing) which appear 2 to 3 minutes after administration of soman. All animals then have tonico-clonic convulsions combined with an opisthotonos. The latent period of the convulsions is approximately 3 to 4 minutes. During this acute phase the animals are cyanosed. Five out of 6 intoxicated animals fall into a coma over approximately 5 to 8 minutes. This coma phase lasts approximately 30 minutes. Complex irregularity of respiratory movements (dyspnea) is observed in 6 animals and heavy secretions are noted. Forty-five minutes after intoxication, 1 animal is still in a coma and only one of the 6 has recovered a normal palpebral reflex and a capacity for the visual ability to follow movement. At the same time, all the animals exhibit persistent tremors combined with significant respiratory rhythm disorders.

EEG Activity

The appearance of the tonico-clonic crises mentioned previously is accompanied by an epileptic state (status epilepticus) which is characteristic of intoxication by organophosphates. This state lasts approximately 5 minutes then ceases during the phase of coma, then reappears (i.e. it lasts for approximately 30 minutes after intoxication). Analysis by frequency bands shows an increase in the EEG energy distribution in the beta band associated with a fall of energy related to the delta band, both on temporal and parietal derivations. This increase of relative energy in the high frequencies is perfectly characteristic of the injection of diazepam to animals (Lipp, Arch. Int. Pharmacodyn., 1973, 202, 244–251). Calculation of the EEG index (delta+theta/beta), over the first 45 minutes post-intoxication, shows a very significant reduction of the latter, relative to the period prior to the injection of soman. This demonstrates, according to the data in the literature, a hyperexcitation at a cerebral level (Nagymajtenyi et al., Neurotox. Teratology, 1988, 10, 429–434).

From Forty-five Minutes Post-intoxication to the End of EEG Recording (5 Hours Post-intoxication, Period $P_2$)

Clinical Signs

The 3 animals not receiving gacyclidine show persistent tremors combined with a clonisms over several hours, as well as of disorders of the respiratory rhythm combined with complex irregularity of abdominal movements. Their recovery is very slow, as 1 single animal in 3 shows biting and clutching reflexes as well as a visual abilty to follow movement 6 hours after intoxication. Respiratory disorders combined with a hypersecretion are noted during all of period $P_2$. One of the animals dies from respiratory distress 4 hours after intoxication.

In the animals receiving gacyclidine, a cessation of clonisms or tonico-clonic crises is noted 5 to 10 minutes after i.v. injection of the product, as well as a complete disappearance of respiratory disorders. The animals have a regular respiration. After the initial coma phase, the 3 animals treated with gacyclidine recover their capacities for biting, clutching and visual ability to follow movement, 2 hours to 2 hrs 30 min after intoxication. None of the 3 animals treated with gacyclidine dies during the first 5 hours following injection with soman.

EEG Activity

In animals not receiving gacyclidine, a persistence of epilepticus status is noted for 2 hrs 30 min to 3 hours after intoxication. EEG activity then decreases gradually with a)—a predominance of relative energy in the low frequencies (delta bands) combined with b)—a decline in the relative energy in the high frequencies (beta bands). Calculation of the EEG index during period $P_2$ shows, relative to the period preceding injection of soman, a strong increase in the latter, both in temporal and parietal derivations. This increase of the index, by an increase in the relative part of the delta band and fall in that of the beta band, is predicative of neuropathological after-effects (Philipens et al., Pharmacol. Biochem. Behav., 1992, 42, 711–719).

In the animals receiving gacyclidine, it is noted that the status epilepticus stops 8 to 10 minutes after the i.v. injection of this product. The high frequencies/high energy trace gives way to a slow wave trace (2–4 Hz) characteristic of gacyclidine for approximately 1 hour. The EEG trace then gradually returns to normal without resumption of paroxysm activity. Analysis by frequency band over period $P_2$ shows a distribution of EEG energy equivalent to that recorded over the period preceding intoxication. The EEG index calculated during this period is identical to that of the pre-intoxication period.

From Five Hours Post-intoxication to Sacrifice of the Animals (3 Weeks After the Experiment)

The 2 surviving control animals recover very slowly after they are returned to their cage. One of the 2 animals dies 48 hours after the experiment in a state of extreme exhaustion (the animal was incapable of moving and feeding itself). The only surviving animal of the control series exhibits a perfectly satisfactory recovery from the fifth hour post-intoxication, combining ocular reflex, clutching, biting, walking, climbing and feeding.

In the 3 animals treated with gacyclidine, total clinical recovery is noted 5 hours after intoxication, except for the capacity to walk and climb which does not return to the normal in these animals until the day after the experiment. None of the 3 animals treated with gacyclidine died during the 3 weeks of observation and their clinical recovery is perfectly satisfactory.

Histopathological Examination of the Brain of the Surviving Animals

Histopathological examination of the brain of the single animal surviving from the control group, which was not treated with gacyclidine, shows neuropathological after-effects in the hippocampus and in the frontoparietal cortex. In the hippocampus, neuronal depopulation foci are noted in the pyramidal layer of the $CA_1$ area, as well as a severe attack on the granular stratum of the gyrus dentatus. In the frontoparietal cortex, a neuronal rarefaction of the II–III layer is noted.

In the animals treated with gacyclidine, no pathological lesion is detected.

2c) Summary See table on the next page.

2d) Conclusion

In this second series of experiments, carried out under conditions which are close to a real situation, it has been possible to show that the administration of gacyclidine, combined with an autoinjectable syringe, a)—very clearly improves the survival of intoxicated animals b)—encourages their clinical recovery c)—rapidly normalizes their EEG activity d)—totally prevents occurrence of neuropathological after-effects.

Therefore, our results clearly demonstrate the therapeutic benefits linked to the administration of gacyclidine in a seriously intoxicated subject who would only have been able to self-administer a single syringe with three compartments, even if the administration of gacyclidine is only carried out 45 minutes after the emergency treatment.

|  |  | Tonic-clonic spasms | EEG | Respiratory problems | Coma | Clinical recovery | Survival to 48 h | Histology at 3 weeks |
|---|---|---|---|---|---|---|---|---|
| Period P1 First 45 minutes after poisoning and injection of atropine/ pralidoxime/diazepan mixture | | violent 3 to 4 minutes after poisoning | Generalised convulsion 3 to 4 minutes after poisoning ↓ delta band ↓ beta band EEG index ‖ | Substantial dyspnoea associated with hypersecretion | 5 to 8 minutes after poisoning in 5 animals | Practically none | | |
| Period P2 beyond 45th minute after poisoning | CONTROL animals | Persistent for several hours | Resumption of general convulsions on leaving coma for about 3 h, then disturbed plot ↓ delta band ↓ beta band EEG index ‖ | Persistent for several hours | Up to 30 minutes after poisoning | Very slow recovery of reflexes and visual following >6 hours | 1/3 | Lesions in the hippocampus and in the frontal-parietal cortex |
| | Animals TREATED with cis-thienylcyclo hexylamine | Cease 5 to 10 minutes after injection of cis-thienyl-cyclohexyl-amine | General convulsions cease in 10 minutes. Slow waves for 1 h then normal EEG plot Normal EEG index | Cease 5 to 10 minutes after injection of cis-thienyl-cyclohexyl-amine | Up to 30 minutes after poisoning | Reflexes and visual following recovered in 2 to 2.5 h after poisoning | 3/3 | No lesions |

3) Third Series of Experiments

The series of experiments described hereafter the value of gacyclidine in the medical support of subjects neither pre-treated nor receiving immediate emergency therapy. The protocol adopted is as follows:

Seven male Cynomolgus monkeys weighing 6–8 kg were used for determination of the efficacy of atropine/diazepam/pralidoxine versus atropine/diazepam/pralidoxine plus gacyclidine. Animals were housed individually until the day of the experiment. One month before the soman challenge, animals were deeply anesthetized with ketamine (20 mg/kg ; i.m.) and prepared for EEG recordings. Gold electrolyzed monopolar screws were implanted over the somatomotor, somesthetic and visual areas. Screws were connected to a 19-contact connector and were embedded with dental cement. Post operative systemic antibiotic (Totapen 1 g/day for 10 days) and local antiseptic (5% Hibitane) post surgical treatments were administered for 4 weeks.

3a) Experimental Protocol

EEG Analysis

After a one month recovery period, the animals were placed on a restaining chair and connected to an EEG recorder. EEG activity was also processed continuously for 6 hours for 1 hour before soman poisoning until 5 hours after on a computer allowing real-time total EEG power determination.

Intoxication and Treatments

Animals were injected, 1 hour after their installation on the restraining chair, with 2 $LD_{50}$ of soman (7.2 mg/kg; i.m.); Von Bredow et al., 1990). Primates were treated, 30 minutes (n=5) or 45 minutes (n=2) after poisoning, as during an emergency situation, with separated iv injections of atropine sulfate (0.05 mg/kg), pradiloxine (6 mg/kg) and diazepam (0.15 mg/kg). The duration of each iv injection was 2 minutes. The doses of atropine, pradiloxine and diazepam used in this study can be considered to be equivalent to those recommended for the treatment of intoxication in humans (Dorosz, Guide pratique des medicaments, Maloine, Parsi pp1–1659, 1995), taking into account the fact that monkeys are about 4 times less sensitive to the effects of atropine than man (Green, 1979). As recommended for humans, in injections of atropine were repeated every 10 minutes. This was performed for 30 minutes (total of 4 injections of atropine). At the time of the second injection of atropine (i.e. 10 minutes after the start of medical intervention), some animals (2 to 5 animals treated 30 minutes after intoxication and 1 of the 2 animals treated 45 minutes after poisoning) also received an intravenous injection of gacyclidine at a dose of 0.1 mg/kg, within the range of therapeutic doses currently tested in man in neurotraumatology.

Observations of the Animals

The animals were closely and continuously observed for the first 5 hours after poisoning. Acute signs of toxicity specifically monitored included tremors, clonic jerks or convulsions, respiratory disturbances, unconsciousness and hyperreactivity in response to sensory stimuli. These signs were noted over 12 time intervals: 2 minutes, 5 minutes, 10–15 minutes, 30 minutes, 45 minutes, 1 hour, 1h15, 1h30, 1h45, 2 hours, 3–4 hours, 4–5 hours following soman challenge. Recovery was assessed at the same times by eyelid reflex, biting reflex, grasping and visual tracking. After this 5-hour-observation phase, EEG recording was stopped and animals were removed from the restraining chair without anesthetic treatment. They were placed in their cages and signs of toxicity and recovery (same as above) were noted at 1, 2, 3, 4 days and 1, 2, 3 weeks after poisoning. Since the primates were free to move in their cages, a) toxicity was also assessed by any prostration of each animal and b) recovery was also evaluated by the capacity of the animals to sit, walk and climb, at each observation time.

Hispatological Examination

Five weeks after soman-challenge, all animals were sacrified by iv injection of high dose of sodium pentobarbital (25 mg/kg). The entire brain was collected for histopathological examination. Tissues were immersed in 10% neutral formalin for 4 weeks and were then processed by routine paraffin embedding methods. Five to 8 mm sections were stained with hemotoxylin and eosin. Brain sections included frontal cortex, entorhinal cortex, amygdala, caudate, hippocampus, thalamus, midbrain, pons, medulla and cerebellum. Tissues were compared to those of non-intoxicated primates.

3b) Results
Before iv Injections of Atropine Pralidoxine and Diazepam

Within minutes, in 6 of 7 intoxicated animals, exposure to 2 $LD_{50}$ of soman produced classical signs of deep anticholinesterase intoxication including abundant salivation, chewing, tremors progressively leading to tonic-clonic convulsions about 12 minutes after poisoning. The development of convulsions was concomitant with the onset of severe status epilepticus. All 6 animals then rapidly became unresponsive and unconscious with 20 to 30 minutes. Anarchic respiratory dyspneic movements were observed in the 6 animals form 30 minutes to 2 hours after poisoning. The EEG activity of these 6 animals showed that convulsions were accompanied by seizures with continuous high voltage/spike activity (see FIGS. 1–2, periods A and B). EEG energy was markedly increased compared to the period preceding intoxicaiton (2.5 to 3 fold basaline values (see FIGS. 1–2, periods A and B).

In 1 of the 7 intoxicated primates, soman poisoning induced tremors and then tonic-clonic convulsions (latency 16 minutes), but with no loss of consciousness and comatose state (persistence of biting-and grasping-reflexes and visual tracking capacity). Convulsions were associated with less severe status epilepticus (only low voltage spike activity (see FIG. 3, periods A and B) than the previously described for the other 6 primates. The variation of the EEG power of this animal therefore showed only a 1.5 fold increase of energy between periods A and B (see FIG. 3). This last animal received classical medical support, without gacyclidine, 30 minutes after intoxication.

From iv Injections of Atropine, Pralidoxime and Diazepam Alone or Combined with Gacyclidine Until 5 Hours Post Intoxication
Animals Treated 45 Minutes after Poisoning One of the primates which exhibited severe seizures and convulsions was treated, 45 minutes after intoxication, with iv injections of atropine, pralidoxime and diazepam alone. Seizures were not controlled by this treatment and these animals rapidly died about 1 hour after poisoning, after being totally unreactive with abundant salivation.

An other animal, which also presented severe epileptic activity after soman challenge, was treated with gacyclidine in addition to atropine, pralidoxime and diazepam. Despite these injections, the animals did not recover and remained in a profound comatose state for about 5 hours with total unreactivity except for persistence of eyelid reflex. The cerebral activity of this primate was dramatically altered with seizures lasting about 2h30, followed by a slow progressive return to normal EEG activity. Due to its poor clinical state, this animal was euthanatized by an iv injection of high-dose pentobarbital at the end of the 5-hours observation period.

In view of the limited efficacy of both classical treatments and gacyclidine, when injected to primates 45 minutes after poisoning, the following experiments were carried out with animals receiving treatment 30 minutes after intoxication.
Animals Treated 30 Minutes after Poisoning In 4 primates presenting intense status epilepticus before treatment, iv injections of atropine, pralidoxime and diazepam alone (n=2) or associated with gacyclidine (n=2) were unable to reverse the comatose phase which lasted about 2 hours to 3h30 after poisoning. During this phase, animals did not present convulsions, but remained totally unreactive except for persistence of the eyelid reflex. They then progressively recovered with restoration of biting-, grasping-reflexes and visual tracking capacity about 4–5 hours after intoxication. Gacyclidine was not considered by the observers to accelerate the clinical recovery of the animals, but rapidly restored normal ventilation of the primates 10 to 15 minutes after administration. In comparison, animals receiving atropine, pralidoxime and diazepam alone exhibited profound respiratory disorders for about 2 hours.

The EEG activity of the 2 animals receiving atropine, pralidoxime and diazepam alone, showed continuous seizures with high voltage/spike activity and high EEG enregy (at least twice tha basiline values) which persisted about 1 hour after starting treatment (see FIG. 1, periods C to F). This was followed by a post-critical phase with high voltage/slow-wave pattern lastin about 30 minutes (see FIG. 1, period G). EEG activity then gradually returned to normal pattern until the end of the observation period (see FIG. 1, periods H and I).

Comparatively, in the other 2 animals treated with gacyclidine, in addition ot atropine, pralidoxime and diazepam, continuous seizures with high EEG energy (at least twice baseline values) persisted only 5 to 10 minutes after gacyclidine injection (see FIG. 2, periods C and D). This was rapidly followed by a high frequency/low voltage pattern which lasted about 40 minutes before progressive return of normal EEG activity (FIG. 2, periods E to I). EEG energy, which was more than twice baseline levels during periods C and D, rapidly returned to normal values after return of the typical high frequency/low voltage pattern (FIG. 2, periods E and F).

As previously mentioned, the primate which exhibited less severe status epilepticus after soman poisoning was treated with atropine, pralidoxime and diazepam alone. In this animal, convulsions lasted about 1 hour after poisoning, this primate remained totally reactive throughout the 5-hour observation period (eyelid-, biting-reflexes, viqual tracking). Its grasping reflex was only transiently altered from 1 hour to 3 hours after intoxication. No respiratory disorders were noted during the 5-hour period following intoxication. EEG recordings, showed that the low voltage spike activity, observed in this animal during period B, persisted for about 30 minutes after starting treatment (FIG. 3, periods C to E) and EEG activity then rapidly returned to normal (FIG. 3, period F).
From 5 Hours Post-intoxication Until Sacrifice of the Animals (5 Weeks after Poisoning)

As stated above, clinical recovery of the animals treated with atropine, pralidoxime and diazepam alone or combined with gacyclidine was complete about 4–5 hours after poisoning in terms of reflexes and visual tracking. Just after being returned to their cages, animals receiving injections of atropine, pralidoxime and diazepam alone were able to sit and feed. Their capacity to walk and climb appeared normal on the day after poisoning.

In comparison, primates also treated with gacyclidine remained prostate just after return to their cages. They recovered a sitting position and feeding only one day after intoxication. They were unable to walk and climb before 3 to 4 days after poisoning. All these primates then survived in good clinical state during the 5-weeks observation period.
Histopathological Examination Histopathological examination of the primates presenting intense status epilepticus before treatment revealed neuronal rarefaction 5 weeks after soman-challenge, in the frontoparietal cortex of the 2 animals receiving atropine, pralidoxime and diazepam alone accompanied by marked disappearance of cerebellar Purkinje cells. In contrast, no lesions were observed in the cerebral and cerebellar tissues of the 2 primates who received combined treatment with gacyclidine. cerebral and cerebellar tissues of these two last animals were similar to those of non-intoxicated primates. In the primates which exhibited less severe status epilepticus after soman poisoning and treated with atropine, pralidoxime and diazepam alone, no neuronal rarefaction was observed in the frontoparietal cortex or cerebellum.

3c) Conclusion

The present data demonstrate that classical iv injections of atropine, diazepam and pralidoxime, even combined with iv injection of gacyclidine, were unable to prevent soman-induced toxicity when treatment was delayed 45 minutes after poisoning. In the case of severe OP-poisoning, gacyclidine, injected 30 minutes after intoxication, clearly stops seizures and prevents soman-induced neuropathology, which both persist after administration of atropine, diazepam and pralidoxime alone.

Formulation

| Preparation for an injectable solution of gacyclidine | |
|---|---|
| lyophilisate of gacyclidine | 0.5 mg |
| mannitol | 25 mg |
| sodium chloride | 85.5 mg |
| water for injectable preparations: sqf | 10.0 ml |

The substances which are optionally combined with the thienylcyclohexylamine, are used in their usual forms in their respective pharmacological fields.

What is claimed is:

1. A composition for inhibiting exogenous neurotropic or neurotoxinic compounds comprising an inhibitorily effective amount of 2-methyl-1-(1-piperidinyl)-1-(2-thienyl)-cyclohexane in substantially pure racemic, diastereoisomeric or enantiomeric form and at least one member of the group consisting of an anticonvulsive substance, an anticholinergic substance and a substance which reactivates cholinesterases.

2. A composition of claim 1 wherein the anticholinergic substance is selected from the group consisting of atropine, scopolamine, atropine N-oxide, dihexyverine and tiemonium methylsulfate.

3. A composition of claim 1 wherein the anticonvulsive substance is selected from the group consisting of phenobarbital, primidone, carbamazepine, ethosuximide, phenytoin, sodium valproate, progabide, gabapentin, vigabatrin, loprazolam and a benzodiazepine selected from the group consisting of clonazepam, clobazam, diazepam and prodiazepam.

4. A composition of claim 1 wherein the substance which reactivates cholinesterases is selected from the group consisting of pralidoxime, obidoxime and HI6.

5. A composition of claim 1 wherein the first compound is in its cis diastereoisomeric form.

6. A composition of claim 1 having a reversible cholinesterase inhibitor selected from the group consisting of pyridostigmine and physostigmine.

7. A composition for inhibiting exogenous neurotropic or neurotoxinic effects comprising an inhibitorily effective amount of 2-methyl-1-(1-piperidinyl)-1-(2-thienyl)-cyclohexane in substantially pure racemic, diastereoisomeric or enantiomeric form and at least one anticonvulsive substance, at least one anticholinergic substance and at least one substance which reactivates cholinesterases.

* * * * *